United States Patent
Schmidt

(10) Patent No.: US 10,583,227 B2
(45) Date of Patent: Mar. 10, 2020

(54) FLUID LEVEL SENSOR COVER FOR A MEDICAL WASTE FLUID COLLECTION AND DISPOSAL SYSTEM

(71) Applicant: DORNOCH MEDICAL SYSTEMS, INC., Riverside, MO (US)

(72) Inventor: Craig B. Schmidt, Lenexa, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 380 days.

(21) Appl. No.: 15/276,185

(22) Filed: Sep. 26, 2016

(65) Prior Publication Data
US 2017/0007747 A1    Jan. 12, 2017

Related U.S. Application Data

(62) Division of application No. 13/934,851, filed on Jul. 3, 2013, now Pat. No. 9,474,837.

(51) Int. Cl.
| | | |
|---|---|---|
| *A61M 1/00* | (2006.01) | |
| *G01F 23/72* | (2006.01) | |
| *G08B 21/00* | (2006.01) | |

(52) U.S. Cl.
CPC .......... *A61M 1/0025* (2014.02); *G01F 23/72* (2013.01); *A61M 2205/3382* (2013.01); *A61M 2205/7536* (2013.01); *A61M 2209/10* (2013.01); *G08B 21/00* (2013.01)

(58) Field of Classification Search
CPC ........ A61M 1/0025; A61M 2205/3382; A61M 2205/7536; A61M 2209/10; G01F 23/72
See application file for complete search history.

(56) References Cited

U.S. PATENT DOCUMENTS

| | | |
|---|---|---|
| 3,678,750 A | 7/1972 | Dinoia et al. |
| 3,915,189 A | 10/1975 | Holbrook et al. |
| 4,275,732 A | 6/1981 | Gereg et al. |
| 4,346,711 A | 8/1982 | Agdanowski et al. |
| 4,384,580 A | 5/1983 | Leviton |
| 4,392,860 A | 7/1983 | Huck et al. |
| 4,419,093 A | 12/1983 | Deaton |
| 4,455,140 A | 6/1984 | Joslin |

(Continued)

OTHER PUBLICATIONS

"U.S. Appl. No. 13/934,851, Corrected Notice of Allowance dated Feb. 24, 2016", 7 pgs.

(Continued)

*Primary Examiner* — Kai H Weng
(74) *Attorney, Agent, or Firm* — Schwegman Lundberg & Woessner, P.A.

(57) ABSTRACT

A fluid level sensor assembly for monitoring a fluid level in a fluid collection canister of a medical waste fluid collection system. The fluid level sensor assembly includes a fluid level sensor configured for monitoring the fluid level in the fluid collection canister and a fluid level sensor cover configured for preventing direct contact between the fluid level sensor and a fluid in the fluid collection canister. The fluid level sensor cover includes a polymeric cap and polymeric sheath extending from the cap. The elongate tubular sheath surrounds an elongate probe of the sensor with the cap positioned at a base of a sensor body of the sensor to prevent direct fluid contact with the elongate sensor probe and the sensor body.

18 Claims, 5 Drawing Sheets

(56) References Cited

U.S. PATENT DOCUMENTS

| | | |
|---|---|---|
| 4,460,361 A | 7/1984 | Nichols |
| 4,653,518 A | 3/1987 | Adachi |
| 4,845,986 A | 7/1989 | Hayashi et al. |
| 4,891,980 A | 1/1990 | Kawai et al. |
| 5,470,324 A | 11/1995 | Cook et al. |
| 5,620,428 A | 4/1997 | Hand |
| 5,627,523 A | 5/1997 | Besprozvanny et al. |
| 5,683,371 A | 11/1997 | Hand |
| 5,688,255 A | 11/1997 | Hand et al. |
| 5,741,237 A | 4/1998 | Walker |
| 5,741,238 A | 4/1998 | Bradbury et al. |
| 5,776,118 A | 7/1998 | Seifert et al. |
| 5,776,260 A | 7/1998 | Dunn et al. |
| 5,792,126 A | 8/1998 | Tribastone et al. |
| 5,804,961 A * | 9/1998 | Castillo ............... G01D 5/485 324/207.13 |
| 5,807,359 A | 9/1998 | Bemis |
| 5,871,476 A | 2/1999 | Hand |
| 5,885,240 A | 3/1999 | Bradbury et al. |
| 5,901,717 A | 5/1999 | Dunn et al. |
| 5,931,822 A | 8/1999 | Bemis et al. |
| 5,944,703 A | 8/1999 | Dixon et al. |
| 5,945,004 A | 8/1999 | Ohira et al. |
| 5,960,837 A | 10/1999 | Cude |
| 5,975,096 A | 11/1999 | Dunn et al. |
| 6,056,731 A | 5/2000 | Koetke et al. |
| 6,152,902 A | 11/2000 | Christian et al. |
| D435,906 S | 1/2001 | Wilkinson et al. |
| 6,261,276 B1 | 7/2001 | Reitsma |
| 6,263,887 B1 | 7/2001 | Dunn |
| 6,358,232 B1 | 3/2002 | Hand et al. |
| 6,494,869 B1 | 12/2002 | Hand et al. |
| 6,588,436 B2 | 7/2003 | Dunn et al. |
| 6,626,877 B2 | 9/2003 | Anderson et al. |
| 6,652,495 B1 | 11/2003 | Walker |
| 6,672,477 B2 | 1/2004 | Miller et al. |
| 6,673,055 B2 | 1/2004 | Bemis |
| 6,776,175 B2 | 8/2004 | Dunn et al. |
| 6,796,317 B2 | 9/2004 | Dunn et al. |
| 6,893,425 B2 | 5/2005 | Dunn et al. |
| 7,090,663 B2 | 8/2006 | Dunn et al. |
| 7,115,115 B2 | 10/2006 | Bemis et al. |
| 7,258,711 B2 | 8/2007 | Dunn et al. |
| 7,497,340 B2 | 3/2009 | Hershberger et al. |
| 7,585,292 B2 | 9/2009 | Anderson et al. |
| 7,674,248 B2 | 3/2010 | Anderson et al. |
| 7,879,228 B2 | 2/2011 | Dunn et al. |
| 7,892,420 B2 | 2/2011 | Dunn et al. |
| 8,025,173 B2 | 9/2011 | Michaels |
| 8,292,857 B2 | 10/2012 | Martini et al. |
| 9,474,837 B2 | 10/2016 | Schmidt |
| 2005/0004537 A1 | 1/2005 | Dunn et al. |
| 2005/0010179 A1 | 1/2005 | Dunn et al. |
| 2005/0139532 A1 | 6/2005 | Hershberger et al. |
| 2005/0171495 A1 | 8/2005 | Austin et al. |
| 2005/0187529 A1 | 8/2005 | Reasoner et al. |
| 2007/0135779 A1 | 6/2007 | Lalomia et al. |
| 2008/0053539 A1 | 3/2008 | Hershberger et al. |
| 2009/0005747 A1 | 1/2009 | Michaels et al. |
| 2009/0012485 A1 | 1/2009 | Michaels et al. |
| 2009/0101219 A1 | 4/2009 | Martini et al. |
| 2009/0159535 A1 | 6/2009 | Hershberger et al. |
| 2011/0005312 A1* | 1/2011 | Hopper ............... G01F 23/0046 73/313 |
| 2012/0152016 A1* | 6/2012 | Prinstil ............... G01F 23/68 73/311 |
| 2015/0011953 A1 | 1/2015 | Schmidt |

OTHER PUBLICATIONS

"U.S. Appl. No. 13/934,851, Corrected Notice of Allowance dated May 17, 2016", 2 pgs.

"U.S. Appl. No. 13/934,851, Notice of Allowance dated Feb. 1, 2016", 11 pgs.

"U.S. Appl. No. 13/934,851, Notice of Allowance dated May 17, 2016", 2 pgs.

"U.S. Appl. No. 13/934,851, Notice of Allowance dated Jun. 29, 2016", 7 pgs.

"U.S. Appl. No. 13/934,851, Response filed Nov. 16, 2015 to Restriction Requirement dated Sep. 29, 2015", 8 pgs.

"U.S. Appl. No. 13/934,851, Restriction Requirement dated Sep. 29, 2015", 6 pgs.

"European Application Serial No. 14175435.8, Extended European Search Report dated Oct. 9, 2014", 7 pgs.

"European Application Serial No. 14175435.8, Office Action dated Jan. 12, 2015", 2 pgs.

"European Application Serial No. 141754385.8, Response filed Jul. 7, 2015 to Office Action dated Jan. 12, 2015", 11 pgs.

"European Application Serial No. 14175435.8, Communication Pursuant to Article 94(3) EPC dated Dec. 14, 2017", 6 pgs.

"European Application Serial No. 14175435.8, Communication Pursuant to Article 94(3) EPC dated Jun. 25, 2019", 5 pgs.

* cited by examiner

US 10,583,227 B2

FLUID LEVEL SENSOR COVER FOR A MEDICAL WASTE FLUID COLLECTION AND DISPOSAL SYSTEM

TECHNICAL FIELD

The present disclosure relates generally to systems and methods for collecting biological fluids during medical procedures and, in particular, to a fluid level sensor assembly including a fluid level sensor cover for a medical waste fluid collection and disposal system.

BACKGROUND

Biological fluids and other types of medical waste often must be collected during surgery or other medical procedures. This is typically accomplished using a medical waste fluid collection cart, which may be part of a medical waste fluid collection and disposal system. After collection, the medical waste and contaminated collection components, such as canister lids, and the like, must be disposed of in accordance with rules and regulations imposed by various government and regulatory organizations. The canisters are then cleaned and disinfected for subsequent use.

In some cases, fluids in the canisters, such as medical waste fluid and/or cleaning/disinfecting, fluid may harm the components of the medical waste fluid collection and disposal system. Accordingly, it is desirable to provide structures to prevent direct fluid contact with components of the medical waste fluid collection and disposal system in order to prevent corrosion or other adverse effects of components of the system.

SUMMARY

The disclosure is directed to several alternative designs, materials and methods of manufacturing medical device structures and assemblies, and uses thereof.

Accordingly, one illustrative embodiment is a medical waste fluid collection system. The system includes a fluid collection canister, a manifold configured to allow for fluid transfer into and/or out of the fluid collection canister, a suction tube in fluid communication with the fluid collection canister providing a fluid path to the fluid collection canister for medical waste fluid, and a vacuum port in fluid communication with the fluid collection canister configured to connect the fluid collection canister to a vacuum source to provide a vacuum level in the fluid collection canister for use in collecting medical waste fluid. The system also includes a fluid level sensor attached to a base of the fluid collection canister. The fluid level sensor includes an elongate metal probe extending into an interior of the fluid collection canister from the base of the fluid collection canister and a float assembly moveable along the elongate metal probe. The float assembly includes a magnet configured to generate an electrical pulse traveling down the elongate metal probe indicative of a level of medical waste fluid in the fluid collection canister. The system also includes a fluid level sensor cover formed of a polymeric material surrounding the elongate metal probe and configured to prevent medical waste fluid within the fluid collection canister from directly contacting the elongate metal probe.

Another illustrative embodiment is a fluid level sensor assembly for monitoring a fluid level in a fluid collection canister of a medical waste fluid collection system. The fluid level sensor assembly includes a fluid level sensor configured for monitoring the fluid level in the fluid collection canister and a fluid level sensor cover configured for preventing direct contact between the fluid level sensor and a fluid in the fluid collection canister. The fluid level sensor includes a sensor body having electrical components therein, an elongate sensor probe extending from the sensor body, and a float assembly surrounding the elongate sensor probe and movable relative to the elongate sensor probe along a longitudinal axis of the elongate sensor probe with a change in the fluid level in the fluid collection canister. The fluid level sensor cover includes a cap formed of a polymeric material and an elongate tubular sheath formed of a polymeric material. The cap has a lower end, an upper end and a passage extending therethrough from the lower end to the upper end. The elongate tubular sheath has a first end, a second end, and a lumen extending from the first end toward the second end. The first end is attached to the cap such that the passage of the cap is in communication with the lumen of the elongate tubular sheath and the second end of the elongate tubular sheath is closed. The elongate sensor probe is extendable into the lumen of the elongate tubular sheath through the passage of the cap such that the elongate tabular sheath surrounds the elongate sensor probe.

Yet another illustrative embodiment is a fluid level sensor assembly for monitoring a fluid level in a fluid collection canister of a medical waste fluid collection system. The fluid level sensor assembly includes a fluid level sensor configured for monitoring the fluid level in the fluid collection canister and a fluid level sensor cover configured for (preventing direct contact between the fluid level sensor and a fluid in the fluid collection canister. The fluid level sensor includes a sensor body having electrical components therein, an elongate metal sensor probe extending from the sensor body, and an annular float assembly surrounding the elongate metal sensor probe and movable relative to the elongate metal sensor probe along a longitudinal axis of the elongate metal sensor probe with a change in the fluid level in the fluid collection canister. The fluid level sensor cover includes a cap formed of a polymeric material and an elongate sheath formed of a polymeric material. The cap has a lower end sealed to the sensor body and the elongate sheath extends from the cap, through an opening of the annular float assembly, and surrounds the elongate sensor probe.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
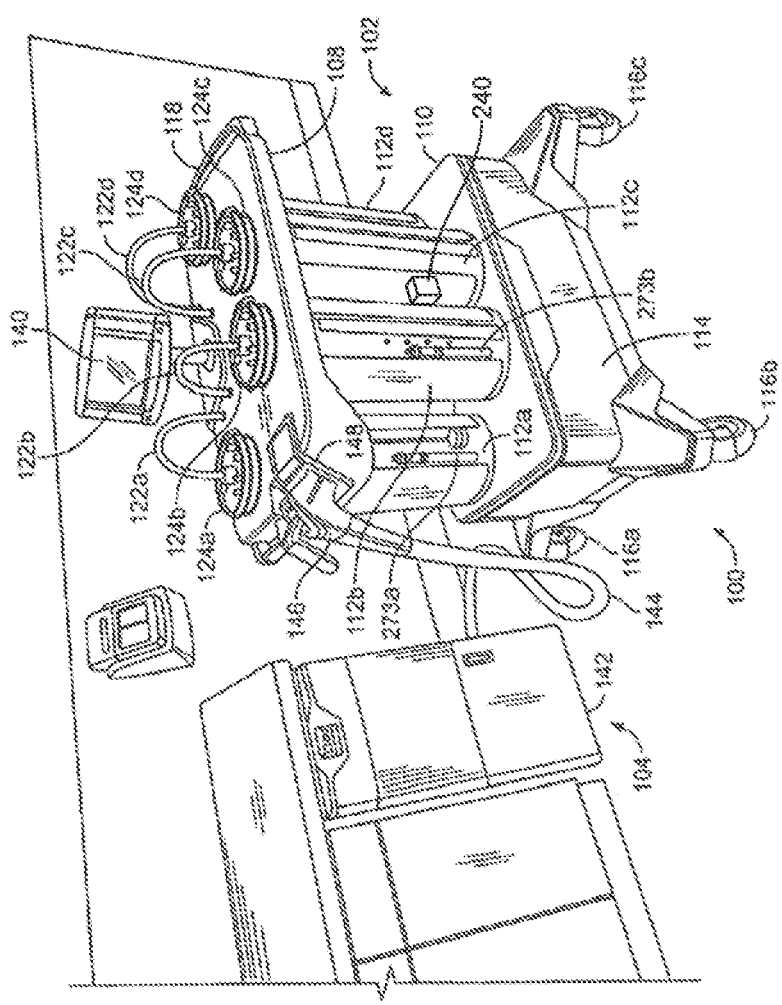
FIG. 1 is a perspective view of a medical waste fluid collection and disposal system including a medical waste fluid collection cart.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DETAILED DESCRIPTION

The following detailed description should be read with reference to die drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a perspective view of a medical waste fluid collection and disposal system 100 including a medical waste fluid collection cart 102 and an evacuation station 104. An illustrative medical waste fluid collection and disposal system, which is not meant to be limiting in any way, is disclosed in, for example: U.S. Pat. No. 8,292,857 filed on Oct. 6, 2008, entitled "MEDICAL WASTE FLUID COLLECTION AND DISPOSAL SYSTEM", the entirety of which is incorporated herein by reference for all purposes. In some cases the medical waste fluid collection cart 102 may include a top plate 108 and a bottom plate 110. Positioned between the top and bottom plates are fluid collection cylinders or canisters 112a-112d. While four canisters are shown in FIG. 1, the medical waste fluid collection cart 102 may include an alternative number of canisters, for example, the medical waste fluid collection cart 102 may be configured to include one canister, two canisters, or another number of canisters, if desired. The medical waste fluid collection cart 102 also may include a bottom cabinet 114 that may be mounted on casters 116a-116d. The casters 116a-116d may be used to provide steering capability for the cart. The casters 116a-116d may include a brake feature. The top plate 108 features a handle 118. As a result, the medical waste fluid collection cart 102 may be easily pushed to and from an operating room.

In some cases, each of the canisters 112a-112d may be connected between a number of corresponding lids 124a-124d via flexible tubing 122a-122d to a vacuum source. The lids may be constructed of molded plastic and may be disposable. The flexible tubing 122a of FIG. 1 may attach at one end to a vacuum port of the lid 124a, with the opposite end attaching to a vacuum pump. The vacuum pump may be provided on the cart 102, or the vacuum tubing may be connected to a vacuum source provided in the medical facility, such as a vacuum pump associated with wall suction provided in an operating room. The vacuum port may be provided with a filter, such as a hydrophobic fitter, positioned in compartment in the lid 124a. A patient suction tube may be connected to a suction port on the lid 124a, while one or more additional ports may be covered by caps. The lid 124a also may include a tubing post for occluded vacuum with the patient tubing. The same applies for the remaining canister lids 124b-124d of FIG. 1. As a result, vacuum or suction is selectively drawn on each canister so that fluids may be collected therein during the medical procedure via the suction tubing extending from the canister to the patient.

The suction and other functions of the medical waste fluid collection cart 102 may be controlled via a user interface 140 (e.g., a touch screen).

After the medical waste fluid collection cart 102 is used in an operating room procedure, and fluids have been collected in one or more of the canisters 112a-112d, the patient suction tubing is removed from the canister lids and all ports for each canister lid 124 to which suction was applied are covered with caps. The medical waste fluid collection cart 102 may then be rolled to a position adjacent to the evacuation station 104 for draining, washing, disinfecting, rinsing and return to a suction collection state, as illustrated in FIG. 1.

The evacuation station 104 may include a housing 142 that contains a source of disinfection solution, pump, drainage system and other components, which are described below, for draining washing and disinfecting the canisters of the medical waste fluid collection cart 102. The evacuation station 104 communicates with the medical waste fluid collection cart 102 by way of the composite hose 144 and the coupler 146. As illustrated in FIG. 1, the coupler 146 is received within a receptacle 148 of the medical waste fluid collection can 102. Washing fluid from the evacuation station 104 may be dispensed in the canisters 112 with cleaning nozzles 273 (nozzles 273a, 273b shown) positioned in the canisters 112 to wash and disinfect the canisters 112.

In some cases, the medical waste fluid collection cart may include a "wash" valve system to facilitate washing and/or disinfecting the canisters 112a-d, a "drain" valve system to facilitate draining fluids from the canisters 112a-d and/or a "vent" valve system to facilitate venting of the canisters 112a-d. The wash valve system, the drain valve system and/or the vent valve system may include one or more valves, one or more valve drive motors for controlling the operation of the valves, one or more tubes for providing fluid transfer to and/or from the canisters 112a-d and one or more electrical components for controlling the operation of the valves and/or valve drive motors. A fluid manifold 240 may be positioned between two or more canisters 112a-112d and may extend into the interior of the cabinet 114. The fluid manifold 240 may include a "wash" tube fitting, a "drain" tube fitting and a "vent" tube fitting. The "wash" tube fitting may communicate with a 3-way "wash" valve and/or the cleaning nozzles 273a, 273b via a fluid passage. The "drain" tube fitting may similarly communicate with a 3-way "drain" valve, via a fluid passage. The "vent" tube fitting may similarly communicate with a 3-way "vent" valve.

When the draining, washing and disinfecting of the cart canisters 112a-112d is complete, the coupler 146 is removed from the receptacle 148 on the medical waste fluid collection cart 102 so that the medical waste fluid collection cart 102 may again be rolled to an operating room for use. The coupler 146 permits a single connection to be made between the medical waste fluid collection cart 102 and the evacuation station 104. This simplifies and expedites connecting the medical waste fluid collection cart 102 to, and disconnecting the medical waste fluid collection cart 102 from, the evacuation station 104. When the medical waste fluid collection cart 102 and the evacuation station 104 are connected using the coupler 146, one or more communication links may be used to permit a controller of the medical waste fluid collection cart 102 and a controller of the evacuation station 104 to communicate so that the user can control both, including one or more of a draining operation, a washing operation and a disinfecting operation, via the touch screen 140.

Figure 2:
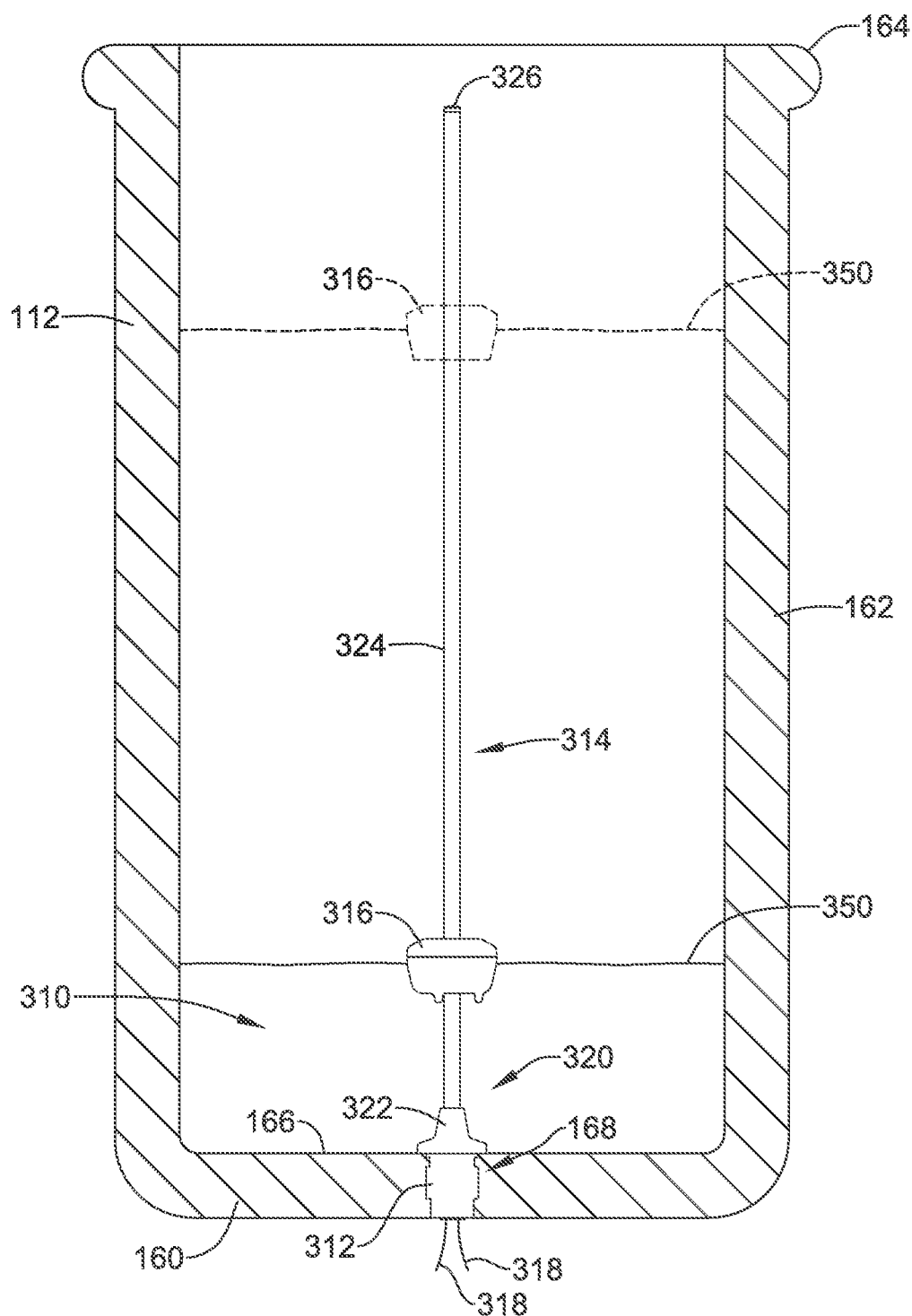
FIG. 2 is a side view of a fluid level sensor assembly in a canister of the medical waste fluid collection cart of FIG. 1 with the canister shown in cross-section.

Turning to FIG. 2, each fluid collection canister 112 may include a base 160 and a sidewall 162, such as a cylindrical sidewall, extending from the base 160 to an upper rim 164 of the canister 112. The base 160 and the sidewall 162 of the canister 112 may define a volume for holding a waste fluid in the canister 112, A fluid level sensor assembly 300 may be assembled with the canister 112 for monitoring the fluid level in the fluid collection canister 112 of the medical waste fluid collection system 100. The fluid level sensor assembly 300 may include a fluid level sensor 310 and a fluid level sensor cover 320 configured to prevent medical waste fluid and/or cleaning/disinfecting, fluid within the fluid collection canister 112 from directly contacting the components of the fluid level sensor 310 (e.g., the elongate sensor probe 314 and/or the sensor body 312).

In some instances, the fluid level sensor 310 may be attached to the base 160 of the canister 112 and extend into the interior of the canister 112 toward the upper end of the canister 112. For example, the fluid level sensor 310 may be a magnetostrictive sensor having a sensor body 312, an elongate metal sensor probe 314 extending from the sensor body 312, and a float assembly 316 (e.g., an annular float assembly) surrounding the elongate sensor probe 314 and axially movable relative to the elongate sensor probe 314 along the longitudinal axis of the elongate metal sensor probe 314. The sensor body 312 may be positioned in a bore 168 in the base 160 of the canister 112 with the sensor probe 314 extending from the sensor body 312 into the interior of the canister 112. A seal 382 (shown in FIG. 3), such as an o-ring seal, may create a fluid seal between the sensor body 312 and the base 160 of the canister 112. The sensor body 312 may include electrical components of the sensor, and the sensor 310 may include electrical wires 318 providing an electrical pathway to/from the electrical components.

The float assembly 316 may move longitudinally along the sensor probe 314 as the fluid level 350 in the canister 112 changes. For example, as shown in FIG. 2, the float assembly 316 may be configured be buoyant in the fluid in the canister 112 such that the float assembly 316 floats on the surface of the fluid. Thus, as the volume of fluid in the canister 112 rises, the float assembly 316 will travel longitudinally along the sensor probe 314. FIG. 2 illustrates the float assembly 316 at a first fluid level 350 (shown in solid lines) and the float assembly 316 at a second fluid level 350 (shown in dashed lines).

Figure 3:
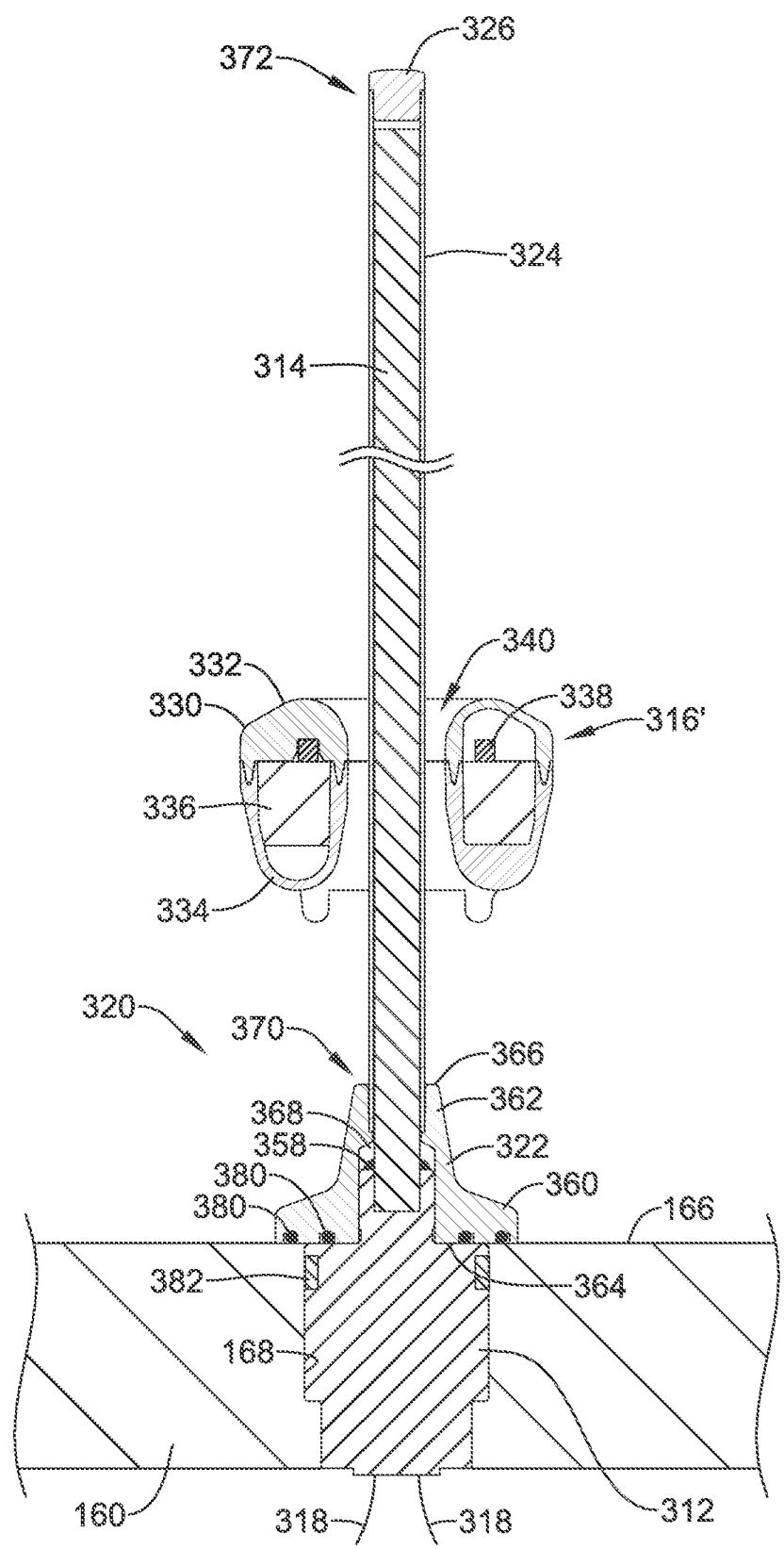
FIG. 3 is a cross-sectional view of the fluid level sensor assembly of FIG. 2.

Referring to FIG. 3, the float assembly 316 may include a housing 330. The housing 330 may include a first, upper housing component 332 and a second, lower housing component 334 which may be attached, such as adhesively bonded or attached with fasteners, to the upper housing component 332. A foam insert 336 or other floatation component may be positioned in the housing 330 to provide and/or increase buoyancy of the float assembly 316. A magnet 338, such as an annular magnet, may also be positioned in the housing 330 such that the magnet 338 surrounds the elongate sensor probe 314. The float assembly 316 may include an opening 340 through which the elongate sensor probe 314 extends through such that the float assembly 316, including the housing 330, the foam insert 336 and/or the magnet 338 may be coaxially disposed around the elongate sensor probe 314.

In operation, an electrical current pulse is passed upward along the elongate metal sensor probe 314 from the sensor body 312, creating a magnetic field around the sensor probe 314. When the magnetic field of the position magnet 338 interacts with the magnetic field around the sensor probe 314, a strain pulse is generated which travels back down the sensor probe 314 toward the sensor body 312 at the speed of sound. The sensor body 312 detects the strain pulse and the position of the magnet 338 (and thus the fluid level 350 at which the float assembly 316 is at) may be determined based on the time the strain pulse takes to reach the detection system in the sensor body 312 to determine the fluid level in the canister 112.

The elongate sensor probe 314 may be attached to the sensor body 312 in any desired fashion. For example, an end portion of the probe 314 may extend into a bore of the sensor body 312. In some instances the end portion of the probe 314 may include threads configured to threadably engage threads of the bore of the sensor body 312. Additionally or alternatively, the elongate sensor probe 314 may be welded to the sensor body 312. For example, a weld 358 may extend circumferentially around the elongate metal sensor probe 314 to weld the elongate sensor probe 314 to the sensor body 312. In some instances, it may be desirable prevent fluid in the canister 112 from directing contacting the metal components of the sensor 312, sensor probe 314 and/or weld 358 in order to avoid corrosion of the metal components. For example, chlorine or other component of a cleaning/disinfectant fluid may harm the metal components.

Figure 4:
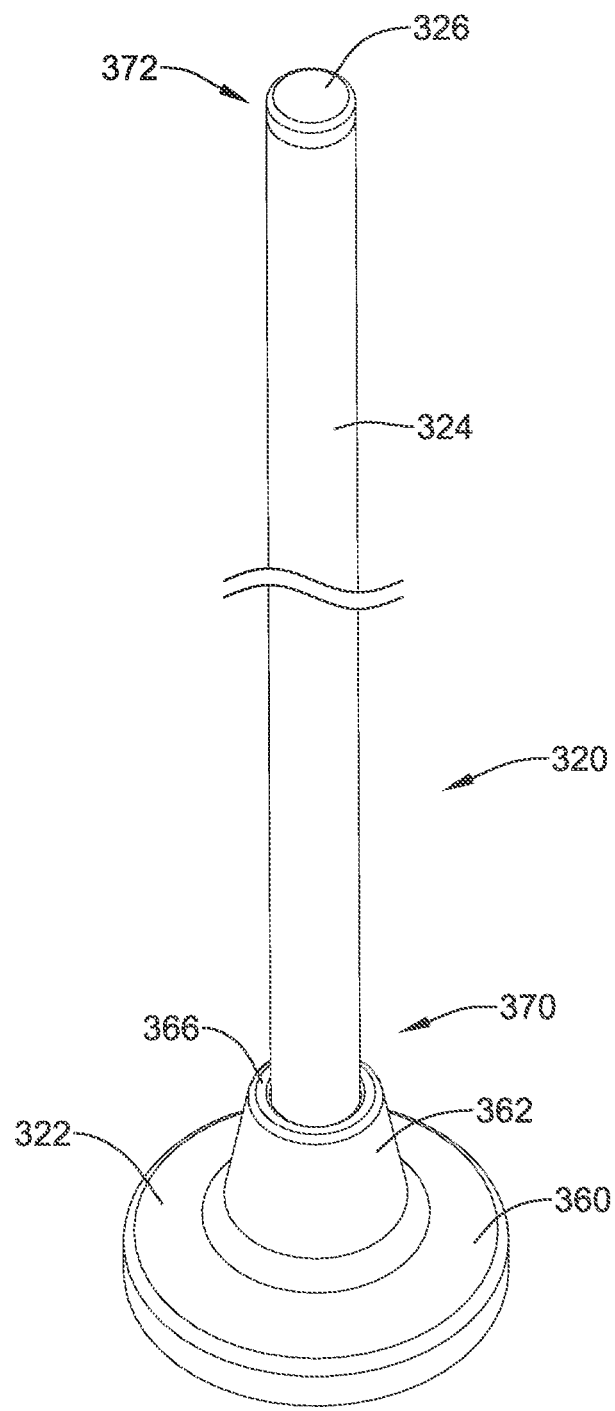
FIG. 4 is a first perspective view of a sensor cover for the fluid level sensor.
Figure 5:
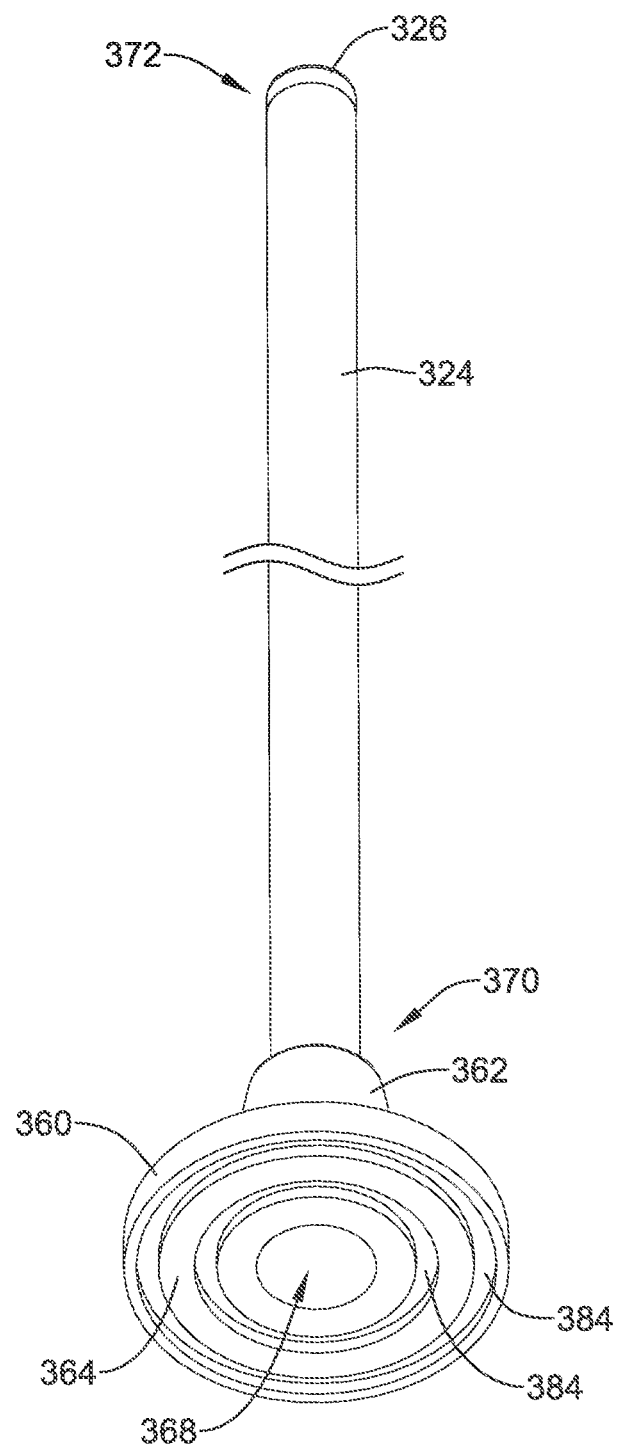
FIG. 5 is a second perspective view of the sensor cover of FIG. 4.

The fluid level sensor cover 320, which may be formed of a polymeric material, may be disposed over the fluid level sensor 210 to prevent medical waste fluid and/or cleaning/disinfecting fluid within the fluid collection canister 112 from directly contacting the components of the fluid level sensor 310 (e.g., the elongate sensor probe 314, the sensor body 312, and/or the weld 358). For example, the fluid level sensor cover 320 may surround the elongate metal probe 312 and the weld 358 and be sealed tightly against an inner surface 166 of the base 160 of the container 112 to prevent fluid from contacting the fluid level sensor 310. An illustrative fluid level sensor cover 320 is shown in FIGS. 4 and 5. The fluid level sensor cover 320 may be formed of any desired polymeric material, such as polyvinyl chloride (PVC), polyamide, polyether, or other desired polymeric material.

The fluid level sensor cover 320 may include a cap 322 and an elongate sheath 324 extending from the cap 322. The cap 322 and/or the elongate shaft 324 may be formed of a polymeric material. The cap 322 may have a lower end 364, an upper end 366 and a passage 368 extending through the cap 322 from the lower end 364 to the upper end 366. The elongate tubular sheath 324 may have a first end 370, a second end 372 and a lumen extending from the first end 370 toward the second end 372. The first end 370 of the tubular sheath 324 may be attached to the cap 322 such that the passage 368 of the cap 322 is in communication with the lumen of the elongate tubular sheath 324. In some instances, the elongate tubular sheath 324 may be formed monolithically with the cap 322 such that the fluid level sensor cover 320 is a unitary structure including the cap 322 and the tubular sheath 324. In other instances, the elongate tubular sheath 324 may be a separate component attached (e.g., adhesively bonded) to the cap 322. For example, a polyvinyl chloride adhesive, or other desired adhesive compatible with the materials of the elongate tubular sheath 324 and the cap 322, may be used to bond the elongate tubular sheath 324 to the cap 322 and seal the joint between the cap 322 and the sheath 324.

The second end 372 of the elongate tabular sheath 324 may be closed such that the lumen of the elongate tubular sheath 324 does not open to the exterior of the elongate tubular sheath 324 at the second end 372. For example, the fluid level sensor cover 320 may include an end cap 326 at the second end 372 of the elongate tubular sheath 324 to close off the lumen at the second end 372. In some instances, the end cap 326 may be a separate component attached to the elongate tubular sheath 324. For example, the end cap 326 may be a plug inserted into the lumen of the tubular sheath 324 to close off the lumen. In other instances, the end cap 326 may be a unitary portion of the elongate tubular sheath 324 formed, molded, or otherwise manufactured to close of the lumen at the second end 372.

The elongate tubular sheath 324 may be disposed around the elongate metal probe 314 to provide a protective barrier between metal probe 314 and the fluid in the canister 112. For example, the elongate tubular sheath 324 may be advanced into the lumen of the tubular sheath 324 through the passage 368 of the cap 322 such that the elongate tubular sheath 324 surrounds the elongate metal probe 314. The weld 358 may be positioned in the passage 368 of the cap 322 with the cap 322 surrounding a base of the sensor body 312, in other instances, the elongate tubular sheath 324 may be molded directly around the elongate metal probe 314 such that the elongate tubular sheath 324 surrounds the elongate metal probe 314 and/or the cap 322 may be molded directly around the base of the sensor body 312. The annular float assembly 316 may surround the elongate tubular sheath 324 and sensor probe 314 such that the elongate tubular sheath 324 and the sensor probe 314 extend through the central opening 340 of the annular float assembly 316. The elongate tubular sheath 324 may have a wall thickness such that the elongate tabular sheath 324 does not affect the travel of the float assembly 316 along the probe 314. For example, the wall thickness of the tubular sheath 324 may be about 0.1 inches, about 0.075 inches, or about 0.05 inches in some instances.

The cap 322 may include a base portion 360 at the lower end 364 and a frusto-conical projecting portion 362 extending from the base portion 360 to the upper end 366 of the cap 322. The frusto-conical projecting portion 362 may be configured to extend into the opening 340 of the float assembly 316 when the float assembly 316 is near the base 160 of the canister 112.

The lower end 364 of the cap 322 may be sealed against the sensor body 312 and/or the inner surface 166 of the base 160 of the canister 112 to prevent fluid in the canister 112 from entering into the passage 368 of the cap 322 or entering into the lumen of the elongate sheath 324. For example, the fluid level sensor cover 320 may include a first seal 380 disposed on the lower end 364 of the cap 322 to seal against the upper surface of the sensor body 312. Additionally or alternatively, the fluid level sensor cover 320 may include a second seal 380 disposed on the lower end 364 of the cap 322 to seal against the inner surface 166 of the base 160 of the fluid collection canister 112. In some instances, the first and/or second seals 380 may be o-ring seals, gaskets, silicone beads, etc. In some embodiments, the second seal 380 may coaxially surround the first seal 380. As shown in FIG. 5, in some instances, the lower end 364 of the cap 322 may include an annular groove 384 configured to receive each of the seals 380.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A fluid level sensor assembly for monitoring a fluid level in a fluid collection canister of a medical waste fluid collection system, the fluid level sensor assembly comprising:
 a fluid level sensor configured for monitoring the fluid level in the fluid collection canister, the fluid level sensor including:
  a sensor body having at least one electrical component therein;
  an elongate sensor probe extending from the sensor body; and
  a float assembly surrounding the elongate sensor probe and movable relative to the elongate sensor probe along a longitudinal axis of the elongate sensor probe with a change in the fluid level in the fluid collection canister; and
 a fluid level sensor cover configured for preventing direct contact between the fluid level sensor and a fluid in the fluid collection canister, the fluid level sensor cover including:
  a cap formed of a polymeric material, the cap having a lower end, an upper end and a passage extending therethrough from the lower end to the upper end;
  wherein the cap includes a frusto-conical projecting portion extending to the upper end of the cap, the frusta-conical projecting portion extendable into the central opening of the float assembly; and
  an elongate tubular sheath formed of a polymeric material, the elongate tubular sheath having a first end, a second end, and a lumen extending from the first end toward the second end, wherein the first end is attached to the cap such that the passage of the cap is in communication with the lumen of the elongate tubular sheath and the second end of the elongate tubular sheath is closed;
 wherein the elongate sensor probe is extendable into the lumen of the elongate tubular sheath through the passage of the cap such that the elongate tubular sheath surrounds the elongate sensor probe.

2. The fluid level sensor assembly of claim 1, wherein the elongate tubular sheath is formed monolithically with the cap.

3. The fluid level sensor assembly of claim 1, wherein the elongate tubular sheath is adhesively bonded to the cap.

4. The fluid level sensor assembly of claim 1, wherein the fluid level sensor cover includes an end cap at the second end of the elongate tubular sheath to close off the lumen at the second end.

5. The fluid level sensor assembly of claim 1, wherein the fluid level sensor cover includes a first o-ring seal disposed on the lower end of the cap configured to seal against an upper surface of the sensor body.

6. The fluid level sensor assembly of claim 5, wherein the fluid level sensor cover includes a second o-ring seal disposed on the lower end of the cap, the second o-ring seal coaxially surrounding the first o-ring seal, the second o-ring seal configured to seal against a surface of the fluid collection canister.

7. The fluid level sensor assembly of claim 1, further comprising:
 a weld extending circumferentially around the elongate sensor probe to weld the elongate sensor probe to the sensor body;
 wherein the weld between the elongate sensor probe and the sensor body is positionable in the passage of the cap.

8. The fluid level sensor assembly of claim 1, wherein the elongate tubular sheath extends through a central opening of the float assembly.

9. A fluid level sensor assembly for monitoring a fluid level in a fluid collection canister of a medical waste fluid collection system, the fluid level sensor assembly comprising
   a fluid level sensor configured for monitoring the fluid level in the fluid collection canister, the fluid level sensor including:
     a sensor body having at least one electrical component therein;
     an elongate metal sensor probe extending from the sensor body and extending continuously across a depth of the fluid collection canister; and
     an annular float assembly surrounding the elongate metal sensor probe and movable relative to the elongate metal sensor probe along a longitudinal axis of the elongate metal sensor probe with a change in the fluid level in the fluid collection canister, the annular float assembly comprising:
       a foam float body; and
       a housing encapsulating a magnet component and the foam float body; and
     a fluid level sensor cover configured for preventing direct contact between the fluid level sensor and a fluid in the fluid collection canister, the fluid level sensor cover including:
       a cap formed of a polymeric material, the cap having a lower end sealed to the sensor body;
       an elongate sheath formed of a polymeric material extending from the cap, through an opening of the annular float assembly, and surrounding the elongate sensor probe; and
       a first o-ring seal disposed on the lower end of the cap configured to seal against an upper surface of the sensor body; and
       a second o-ring seal disposed on the lower end of the cap, e second o-ring seal coaxially surrounding the first o-ring seal, the second o-ring seal configured to seal against a surface of the fluid collection canister.

10. The fluid level sensor assembly of claim 9, further comprising:
   a base of the fluid collection canister to which the sensor body is mounted.

11. The fluid level sensor assembly of claim 9, wherein the at least one electrical component of the sensor body comprises a magnetostrictive sensor.

12. The fluid level sensor assembly of claim 11, wherein the magnet component comprises an annular magnet.

13. The fluid level sensor assembly of claim 12, wherein the annular float assembly further comprises:
   a lower annular housing;
   an upper annular housing connected to the lower annular housing to form an annular interior space in which the annular magnet is disposed; and
   float material disposed in the annular interior space.

14. A fluid level sensor comprising:
   a sensor body;
   an elongate sensor probe extending from the sensor body; the elongate sensor probe comprising an elongate metal body;
   a cap positioned around a junction of the sensor body and the elongate sensor probe, wherein the elongate sensor probe includes a portion protruding from the cap;
   a sheath extending from the cap to surround the portion of the sensor probe protruding from the cap, wherein the cap and the sheath form a barrier to the junction of the sensor body and the elongate sensor probe; and
   a float assembly positioned around the sheath, the float assembly comprising:
     an annular magnet component for electromagnetically interacting with the elongate sensor probe and generating a strain pulse;
     a lower annular housing;
     an upper annular housing connected to the lower annular housing to form an annular interior space in which the annular magnet component is disposed; and
     float material disposed in the annular interior space.

15. The fluid level sensor of claim 14, further comprising a first seal positioned between the cap and the sensor body.

16. The fluid level sensor of claim 15, further comprising an end cap connected to a distal end of the sheath to seal the sheath.

17. The fluid level sensor of claim 14, wherein the float further comprises:
   an annular foam body.

18. The fluid level sensor of claim 17,
   the sensor body comprises a magnetostrictive sensor.

\* \* \* \* \*

UNITED STATES PATENT AND TRADEMARK OFFICE
CERTIFICATE OF CORRECTION

PATENT NO. : 10,583,227 B2
APPLICATION NO. : 15/276185
DATED : March 10, 2020
INVENTOR(S) : Craig B. Schmidt It is certified that error appears in the above-identified patent and that said Letters Patent is hereby corrected as shown below:

On the Title Page

On page 2, in Column 2, item (56) under "Other Publications", Line 17, delete "141754385.8," and insert --14175435.8,-- therefor In the Claims In Column 8, Line 27, in Claim 1, delete "frusta-conical" and insert --frusto-conical-- therefor In Column 9, Lines 6-7, in Claim 9, delete "comprising" and insert --comprising:-- therefor In Column 9, Line 40, in Claim 9, delete "e" and insert --the-- therefor In Column 10, Line 15, in Claim 14, delete "body;" and insert --body,-- therefor In Column 10, Line 43, in Claim 18, after "17,", insert --wherein:--

Signed and Sealed this
Eighth Day of September, 2020

Andrei Iancu
*Director of the United States Patent and Trademark Office*